(12) United States Patent
Ho

(10) Patent No.: US 8,425,479 B2
(45) Date of Patent: Apr. 23, 2013

(54) ORAL DEBRIS REMOVAL DEVICE

(76) Inventor: Thean Aik Derek Ho, Singapore (SG)

( * ) Notice: Subject to any disclaimer, the term of this patent is extended or adjusted under 35 U.S.C. 154(b) by 671 days.

(21) Appl. No.: 12/665,841

(22) PCT Filed: Jun. 22, 2009

(86) PCT No.: PCT/SG2009/000227
§ 371 (c)(1),
(2), (4) Date: Dec. 21, 2009

(87) PCT Pub. No.: WO2010/151223
PCT Pub. Date: Dec. 29, 2010

(65) Prior Publication Data
US 2011/0202021 A1    Aug. 18, 2011

(51) Int. Cl.
*A61M 1/00* (2006.01)
(52) U.S. Cl.
USPC .......................................................... 604/319
(58) Field of Classification Search .................. 604/317, 604/319; 433/32, 85, 140, 216
See application file for complete search history.

(56) References Cited

U.S. PATENT DOCUMENTS

| 4,459,139 | A | * | 7/1984 | vonReis et al. ...................... 96/6 |
| 4,802,851 | A | | 2/1989 | Rhoades |
| 5,152,686 | A | | 10/1992 | Duggan et al. |
| 5,342,196 | A | | 8/1994 | Van Hale |
| 7,144,383 | B2 | * | 12/2006 | Arnett et al. ...................... 604/35 |
| 2003/0004562 | A1 | * | 1/2003 | DiCarlo ........................ 623/1.13 |
| 2003/0143512 | A1 | | 7/2003 | Hirsch et al. |
| 2006/0025494 | A1 | * | 2/2006 | Gasman ........................ 523/120 |
| 2007/0255290 | A1 | | 11/2007 | Pan |

FOREIGN PATENT DOCUMENTS

WO    WO 99/47068    9/1999

* cited by examiner

*Primary Examiner* — Melanie Hand
(74) *Attorney, Agent, or Firm* — Winthrop & Weinstine, P.A.

(57) ABSTRACT

According to one aspect of the invention, there is provided an oral debris removal device including: a suction unit; a tube in fluid communication with the suction unit, the tube having a tip portion adapted to allow introduction of oral debris into the tube via the tip portion; and a light source positioned to illuminate the tip portion of the tube and a region adjacent to the tip portion of the tube. The oral debris removal device may further include a debris collector chamber coupled between an end section of the suction unit and an end section of the tube. The debris collector chamber may include an internal protruding element disposed along an air flow path across a space between the end section of the suction unit and the end section of the tube, the internal protruding element adapted to prevent oral debris and liquid exiting the tube from entering the suction unit.

18 Claims, 11 Drawing Sheets

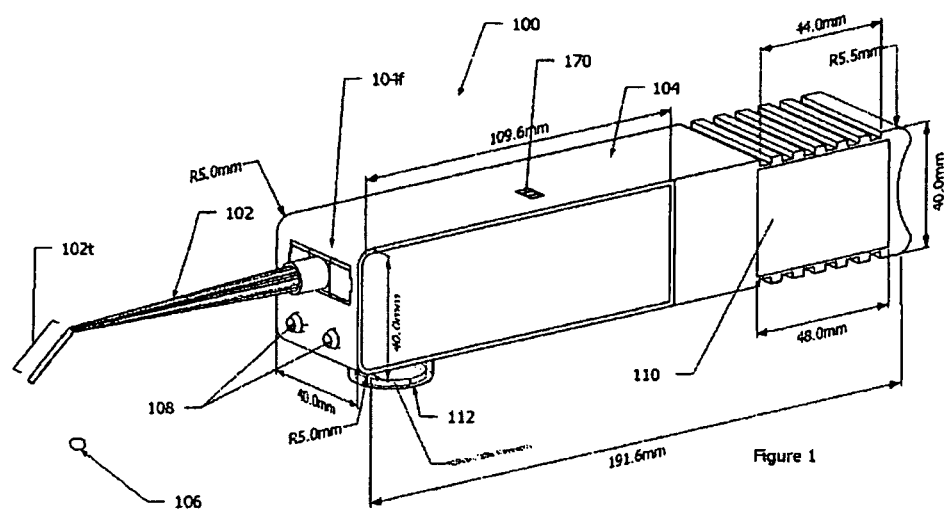
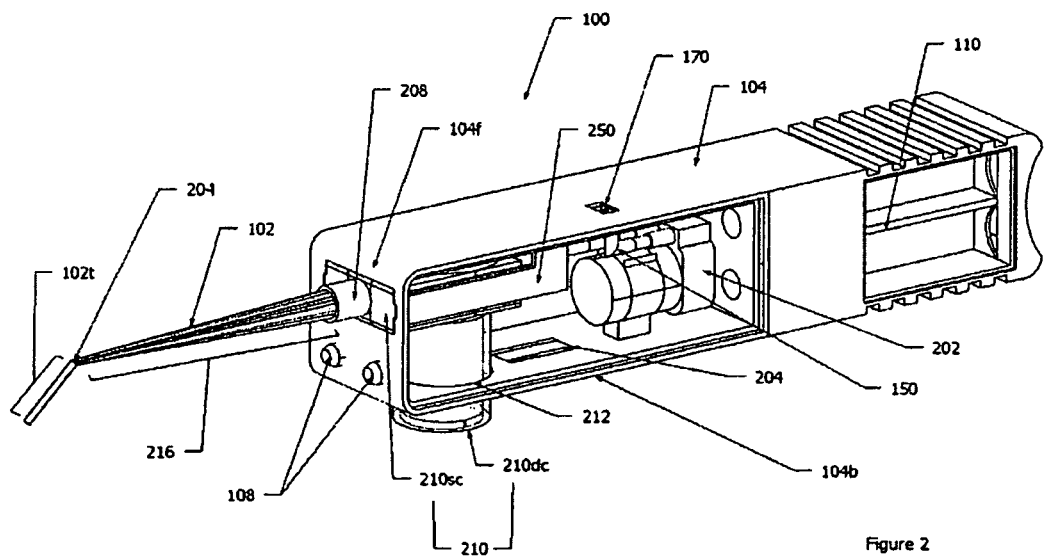

ORAL DEBRIS REMOVAL DEVICE

FIELD OF THE INVENTION

The invention relates to an oral debris removal device.

BACKGROUND OF THE INVENTION

Tonsils are full of indentations, crevices, and folds. These are areas which can trap matter such as bacteria, food particles, dead cells and mucous. This matter collects as debris, which can harden or calcify into white formations called tonsil stones, or commonly known as tonsilloliths. Tonsil stones (tonsilloliths) have been plaguing humans for a long time.

Tonsil stones are sometimes visible in the tonsils as a lump of solid white material, or may sometimes be hidden in the indentations, crevices and folds of the tonsils.

Tonsil stones which are not removed and reside in the tonsils may result in numerous health and social problems. These include:

(i) Bad breath. The mouth provides perfect conditions for bacteria to multiply, whereby the bacteria acts on the debris/tonsil stones to decay the debris/tonsil stones, resulting in particularly bad breath.
(ii) Cough and sore throat. Tonsil stones, providing the food source for bacteria to multiply, can trigger an onset of tonsillitis.
(iii) Ear pain. As the ear and throat share nerve pathways, a person may experience referred ear pain from tonsil stones developing anywhere in the tonsils.
(iv) Tonsil swelling. As more tonsil stones collect within the tonsil, the tonsil itself may swell or become larger.

Known solutions to treat or remove tonsil stones include (i) the removal of the tonsils; (ii) using cotton-swabs, cotton-buds or q-tips to push the tonsil stones out; (iii) using a toothpick or dental pick to dig the tonsil stones out; or (iv) using mouth wash or other oral gargles to mask foul bad breath. However, these solutions are ineffective, or have considerable risks, as outlined in the following paragraphs.

The removal of tonsils, or tonsillectomy, is not a preferred option by most doctors and ENT (ear nose and throat) specialists, unless the circumstances necessitate it. This is because it requires surgery and the associated costs and risks of surgery (as tonsillectomies require the patient to undergo general anesthesia). There is also pain and difficulties in swallowing experienced by the patient following a tonsillectomy. Such procedures also require the aid of third parties (i.e. medical professionals).

Using cotton-swabs, cotton-buds or q-tips may push the tonsil stones deeper into the crevice or folds of the tonsil, thus making the tonsil stone more difficult to remove. Even if the tonsil stone is on the surface of the tonsil, the use of cotton-swabs or buds may merely push the tonsil stone to the back of the throat, where the tonsil stone would need to washed down the throat for the stomach to digest. There is a risk also that the cotton-swabs, the cotton-buds or the q-tips may be dropped down the throat.

There is a risk that the sharp end of the toothpick or dental pick may pierce the tonsils and cause lacerations which result in bleeding. This increases the risk of infections given the presence of bacteria at the site of the tonsil stone. The toothpick or the dental pick also may have the same drawbacks associated with the cotton-swab, the cotton-bud or the q-tip. Using a toothpick or dental pick may also result in breaking-up of a tonsil stone, which may result in added surface area for bacteria to cultivate.

The use of mouth wash or other oral gargles merely treats the symptoms of tonsil stones, specifically, the presence of bad breath. It does not remove the actual tonsil stone which will continue to reside in the tonsil.

Thus, the solutions available do not allow a person who has tonsil stones to safely remove the whole tonsil stone without causing pain or inflicting upon oneself injury or infection.

US patent application no. 2007/0255290 discloses a tonsillith removing device. The device has a tube which is connected to an electric fan, where the electric fan creates suction force so that the tube can remove tonsil stones. However, the device is not portable as it is powered through an electric plug which is connected to power mains. The tip of the tube of the device also does not allow for degree of movement which would allow for the tube of the device to be inserted at different angles into the mouth. Degree of movement is necessary as crevices and holes may occur on any face of the tonsil, and the crevices and holes in the tonsils do not have similarly located or angled entrances. A person using the device may, in the process, overturn the device when trying to maneuver the device to reach his tonsils due to the tube being fixated at one angle. Overturning the device would result in saliva collecting in the device retention area and subsequently being sucked into the electric fan, thereby possibly short-circuiting the device and causing an electric shock to the user.

It would thus be desirable to have a device that is able to remove tonsil stones from the tonsil in a way which does not cause lacerations and does not require the help of a third party. It would also be desirable for the device to be portable and not confined to operate in the vicinity of power mains.

SUMMARY OF THE INVENTION

According to one aspect of the invention, there is provided an oral debris removal device including: a suction unit; a tube in fluid communication with the suction unit, the tube having a tip portion adapted to allow introduction of oral debris into the tube via the tip portion; and a light source positioned to illuminate the tip portion of the tube and a region adjacent to the tip portion of the tube.

The oral debris removal device may further include a housing, upon which the suction unit is provided.

The suction unit may be disposed within the housing.

The suction unit may be connected to the housing.

The suction unit may include any one or more of a diaphragm pump and a vacuum pump.

The oral debris removal device may further include a debris collector chamber coupled between an end section of the suction unit and an end section of the tube.

The debris collector chamber may include a first opening to couple the debris collector chamber to the suction unit; and a filter covering the first opening.

The debris collector chamber may include an internal protruding element disposed along an air flow path across a space between the end section of the suction unit and the end section of the tube, the internal protruding element adapted to prevent oral debris and liquid exiting the tube from entering the suction unit.

The tube may be connected to the housing.

The tube may include a first portion; and a connecting portion disposed between the tip portion of the tube and the first portion, the connection portion allowing misalignment between the tip portion and the first portion.

The tip portion of the tube may include a first portion and a second portion, wherein a longitudinal axis of the first portion is misaligned relative to a longitudinal axis of the second portion.

The connection portion may be made from flexible material.

The first portion of the tube and the tip portion of the tube may be made from resilient or rigid material.

The oral debris removal device may further include a battery compartment, the battery compartment being electrically coupled to both the suction unit and the light source.

The battery compartment may be disposed within the housing.

The light source may be disposed adjacent to the tube.

The light source may include a light emitting diode.

At least a portion of an exterior of the housing may be provided with an anti-slip surface.

The anti-slip surface may include any one or more of a plurality of ridges or a layer of rubber.

The oral debris removal device may further include a variable resistive element electrically coupled to the suction unit, wherein the variable resistive element controls an input power to the suction unit.

The variable resistive element may be an electrical resistor.

The housing may further include an exhaust port, the exhaust port disposed downstream of the suction unit.

The exhaust port may be disposed between the anti-slip surface of the housing and where the tube is connected to the housing.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which:

FIG. 1 is a perspective view of an oral debris removal device, according to one embodiment of the present invention.

FIG. 2 is a perspective view showing the internal components of the oral debris removal device shown in FIG. 1.

DETAILED DESCRIPTION

Figure 3:
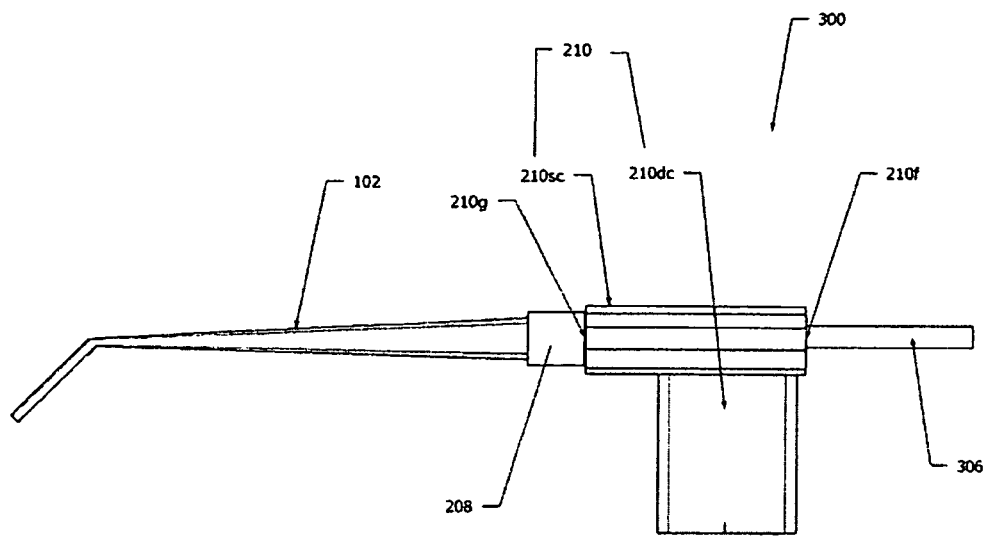
FIG. 3 is a perspective view of a tube unit of the oral debris removal device shown in FIGS. 1 and 2.

While embodiments of the invention will be shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

It will be appreciated that common numerals, used in the relevant drawings, refer to components that serve a similar or the same purpose.

FIGS. 1 to 10 relate to an oral debris removal device 100 according to one embodiment of the present invention.

FIG. 1 is a perspective view of the oral debris removal device 100.

The oral debris removal device 100 is a handheld portable device having suction capability. The oral debris removal device 100 is adapted to provide sufficient suction force to remove tonsilloliths and oral debris (for example, food particles and mucous) from the tonsils and other parts of a mouth. Tonsil stones 106 may be removed from the tonsils (not shown) of a human mouth in a safe way without causing lacerations to the tonsils. The oral debris removal device 100 is designed for self-use (i.e. not requiring the help of a third party) by being operable using one hand and having an integrated light source 108 (e.g.: a light emitting diode, or LED). The integrated light source 108 allows illumination of dark crevices, especially located towards the back of a user's mouth, and also allows the oral debris removal device 100 to be operable with one hand without the need of another hand to hold a separate light source.

The removal of tonsil stones provides less conducive areas for bacteria growth and reduces the incidence of tonsillitis and bad breath associated with tonsil stones.

The oral debris removal device 100 allows a person to remove debris which is stuck in his/her tonsils by providing adjustable suction power created by a suction unit (described in further detail later) within the oral debris removal device 100. Suction occurs through a tube 102 removably attached to an end 104f of a housing 104 for the oral debris removal device 100. The tube 102 has a flexible tip portion 102t, thereby facilitating manipulation and bending by a user to place the tip portion 102t of the tube 102 to the location of a tonsil stone 106. The tonsil stone 106 is removed via the suction created by the suction unit. The tonsil stone 106 is either lodged at an opening of the tip portion 102t of the tube 102 and remains there due to the suction force, or is sucked through the tube 102 and collected inside the housing 104 at a debris collector 112. An opening 170 is provided on the housing 104. The opening 170 is for an exhaust port 150 (see FIG. 2), which is disposed downstream of the suction unit. The exhaust port 150 is for the expulsion of air from the suction unit, when the suction unit is in operation.

The tip portion 102*t* and the suction unit arrangement may allow the tonsil stone 106 to be removed intact, where the tonsil stone 106 may be used for medical examination purposes or for collection by users who are fascinated by the smell of the tonsil stones. The tip portion 102*t* is less abrasive and damaging to the tonsils compared to using toothpicks or dental picks to remove tonsil stones. Further, tonsil stones located deep within crevices and holes in the tonsils may be removed quickly and effectively due to the degree of movement provided by the flexible tip portion 102*t* which allows the tube 102 to reach deeper into the crevices and the holes in the tonsils. The degree of movement provided by the flexible tip portion 102*t* will also allow the tube 102 to reach tonsil stones which are lodged in crevices and holes which are located at different locations on the tonsils.

For instance, when a vacuum pump is used for the suction unit, a vacuum is created at the tip 102*t* of the tube 102. The suction force created by the vacuum at the tip portion 102*t* will allow a person to remove debris which is stuck in the person's tonsils by placing the tip portion 102*t* at the location of the tonsil stone.

A light source 108 is provided at the end 104*f* of the housing 104, wherein the light source 108 is directed to illuminate the tip portion 102*t* of the tube 102. In FIG. 1, the light source 108 is shown to be disposed adjacent to the tube 102, although it is also possible to mount the light source 108 at another location as long as the light source 108 can illuminate the tip portion 102*t* of the tube 102. Power for the light source 108 and the suction unit is provided by a battery (not shown in FIG. 1 for the sake of simplicity) in a battery compartment 110 of the housing 104. By having its own battery compartment 110, the oral debris removal device 100 is portable and therefore the user is not restricted to operating the oral debris removal device 100 in the vicinity of power mains.

FIG. 2 is a perspective view showing the internal components of the oral debris removal device 100 shown in FIG. 1.

The housing 104 contains the fixtures for the various components of the oral debris removal device 100, such as a battery compartment 110, a suction unit 202 (which may be a vacuum pump), a variable switch 204, electrical connections (not shown for the sake of simplicity), a light source 108, a tube adaptor 208, and a debris collector chamber 210. The housing 104 has an opening at one end 104*f* to slide a separator chamber 210*sc* of the debris collector chamber 210 into the housing 104. Guide rails 250 are provided inside the housing 104 to facilitate insertion of the separator chamber 210*sc* into the housing 104. The tube 102 may be connected, for example through screwing, onto the separator chamber 210*sc*. Another opening 212 on a bottom wall 104*b* allows insertion of a debris collector 210*dc* of the debris collector chamber 210 into the housing 104. The housing 104 may be made up of a hard plastic casing.

The oral debris removal device 100 is provided with a suction unit 202. In FIG. 2, it is shown that the suction unit 202 is disposed within the housing 104, although it would also be possible to connect the suction unit 202 to the housing 104. A suitable device such as a diaphragm pump or a vacuum pump may be used for the suction unit 202.

The tube 102 is in fluid communication with the suction unit 202. The tube 102 has a tip portion 102*t* adapted to allow introduction of oral debris into the tube 102 via the tip portion 102*t*. A light source 108 is positioned to illuminate the tip portion 102*t* of the tube 102 and a region adjacent to the tip portion 102*t* of the tube 102. Thus, for example, when the tube 102 is in contact with the tonsils, the portion of the tonsils that is adjacent to the area of contact will also be illuminated by the light source 108.

The debris collector chamber 210 is coupled between an end section of the suction unit 202 and an end section of the tube 102. The debris collector chamber 210 has a first opening 210*f* (shown more clearly in FIG. 3) to couple the debris collector chamber 210 to the suction unit 202 via a pump connector 306 (shown more clearly in FIG. 3) and a filter 708 (shown more clearly in FIG. 7). The filter 708 traps microparticles of dust which can shorten the lifespan of the suction unit 202.

The debris collector chamber 210 further includes a second opening 210*g* (shown more clearly in FIG. 3) which allows the tube adaptor 208 and the tube 102 to be connected to the separator chamber 210*sc*, for example through screwing.

The debris collector chamber 210 may be provided as an integrated unit, although it is described with reference to FIG. 2 that the debris collector chamber 210 is provided in two portions, a separator chamber 210*sc* and a debris collector 210*dc*. The first opening 210*f* of the debris collector chamber 210 may be provided on the separator chamber 210*sc*. A removable debris collector chamber 210, which may be further dismantled into its separator chamber 210*sc*, and its debris collector 210*dc*, allows the parts of the oral debris removal device 100 that come into contact with oral debris to be washed and cleaned separately from the electrical components (e.g. the suction unit 202) of the oral debris removal device 100, preventing water damage to the electrical components.

While the tube 102 is shown in FIG. 2 to be connected to the separator chamber 210*sc*, the tube 102 may also be connected to the housing 104. It will be appreciated that it is sufficient that the tube 102 is connected to be in fluid communication with the suction unit 202. In FIG. 2, the tube 102 is in fluid communication with the suction unit 202 via the debris collector chamber 210. The tube 102 is connected to the debris collector chamber 210 via the tube adaptor 208.

The tube 102 may be made of hard clear plastic having an area of inflexion 204 near the tip 102*t* of the tube 102. The inflexion area 204 provides the tip 102*t* with a degree of movement relative to a main portion 216 of the tube 102 to be adjusted. The tip 102*t* of the tube 102 may be convex shaped.

FIG. 3 is a perspective view of a tube unit 300 of the oral debris removal device 100 shown in FIGS. 1 and 2.

The tube unit 300 includes the tube 102, the tube adaptor 208, the debris collector chamber 210 and a pump connector 306.

The debris collector chamber 210 includes the separator chamber 210*sc* and the debris collector 210*dc*. The pump connector 306 facilitates coupling between the filter 708 (see FIG. 7), suction unit 202 (see FIG. 2) and the debris collector chamber 210, whereby the pump connector 306 is integrated with the debris collector chamber 210. Thus, the pump connector 306 provides the first opening 210*f* to the debris collector chamber 210. The second opening 210*g* provides another opening to the debris collector chamber 210.

Figure 4A:
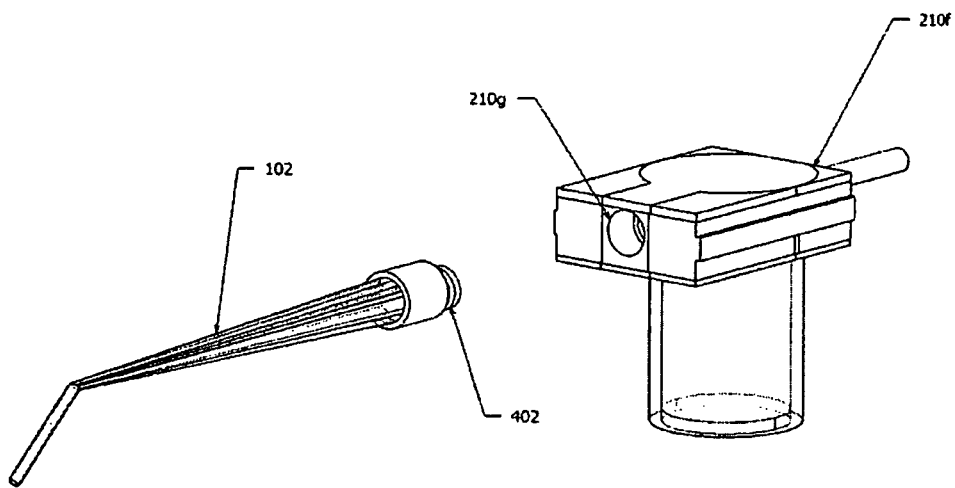
FIG. 4A is another perspective view of the tube unit shown in FIG. 3.

FIG. 4A is another perspective view of the tube unit 300 shown in FIG. 3. FIG. 4A, shows that the tube 102 has a screw thread 402 which facilitates connection of the tube 102 to the second opening 210*g* of the debris collector chamber 210.

Figure 4B:
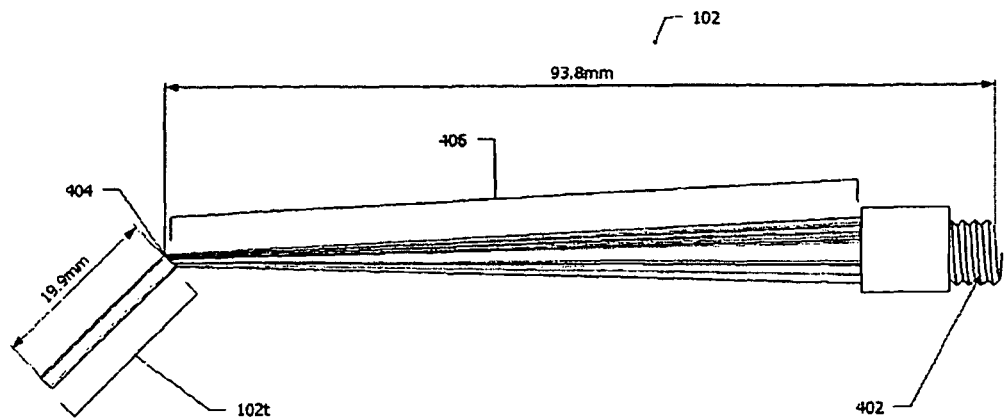
FIG. 4B is a perspective view of a tube of the oral debris removal device shown in FIGS. 1 and 2.

FIG. 4B is a perspective view of the tube 102 of the oral debris removal device 100 shown in FIGS. 1 and 2. The tube 102 comprises a first portion 406; and a connecting portion 404 disposed between the tip portion 102*t* of the tube 102 and the first portion 406. The connection portion 404 allows misalignment between the tip portion 102*t* and the first portion 406.

The connection portion 404 may be made from flexible material. The first portion 406 of the tube 102 and the tip portion 102*t* of the tube 102 may be made from resilient or rigid material.

Figure 5A:
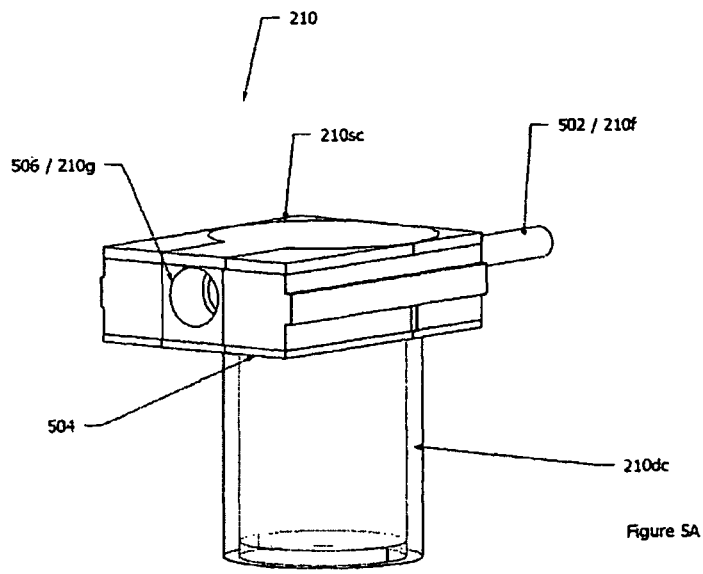
FIGS. 5A and 5B each show a different perspective view of a debris collector chamber of the oral debris removal device shown in FIGS. 1 and 2.
Figure 5B:
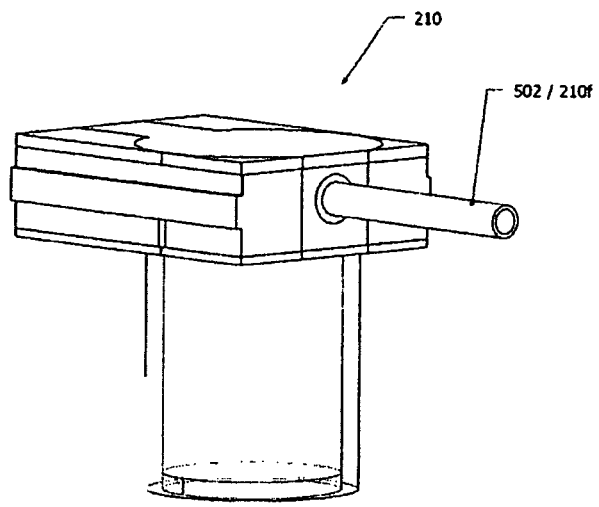

FIGS. 5A and 5B each show a different perspective view of the debris collector chamber 210 of FIGS. 1 and 2.

The debris collector chamber 210 includes the separator chamber 210*sc* and the debris collector 210*dc*.

The separator chamber 210*sc* may be made from hard clear plastic. The separator chamber 210*sc* may have three openings 502, 506 and 504.

The separator chamber 210*sc* ensures that liquid and debris sucked in through the tube 102 (see FIG. 4B) are not sucked immediately into the suction unit 202 (see FIG. 2).

The first opening 502 of the separator chamber 210*sc* is also the first opening 210*f* of the debris collector chamber 210.

The third opening 504 of the separator chamber 210*sc* allows connection of the debris collector 210*dc*, through screwing the debris collector 210*dc* into the separator chamber 210*sc*.

The second opening 506 allows connection of the tube 102 (see FIG. 4B). The second opening 506 of the separator chamber 210*sc* is also the second opening 210*g* of the debris collector chamber 210.

The debris collector 210*dc* may be made of hard clear plastic to allow viewing of debris and liquid collected.

Figure 6:
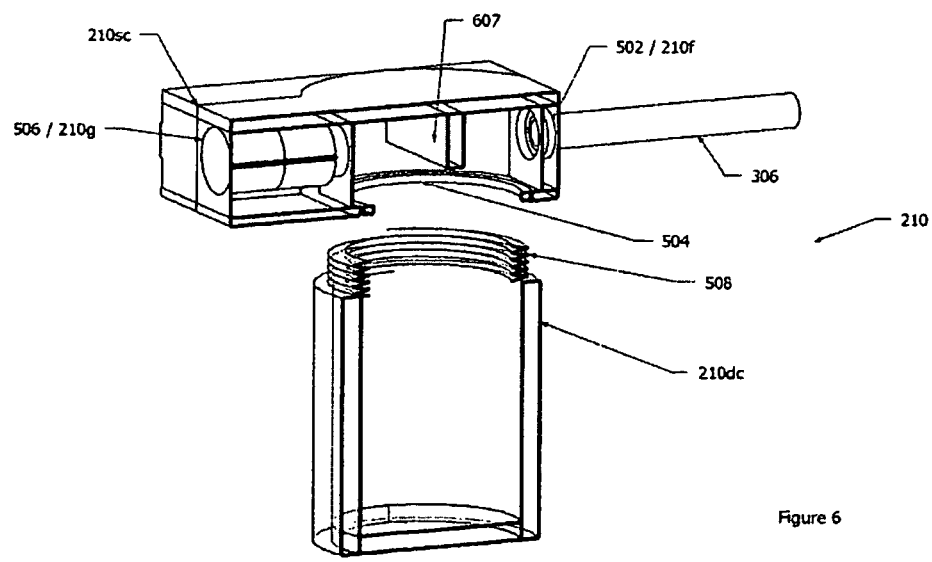
FIG. 6 is a cross-section view of the debris collector chamber of the oral debris removal device shown in FIGS. 1 and 2.

FIG. 6 is a cross-section view of the debris collector chamber 210. The separator chamber 210*sc* ensures that liquid and debris sucked in through the tube 102 (see FIG. 4B) are not sucked immediately into the suction unit 202 (see FIG. 2). An internal protruding element 607 may be disposed between where both the suction unit 202 and the tube 102 (see FIG. 2) are coupled to the debris collector chamber 210. The internal protruding element 607 may be disposed along an air flow path across a space between the end section of the suction unit 202 and the end section of the tube 102. The internal protruding element 607 is adapted to prevent oral debris and liquid exiting the tube 102 from entering the suction unit 202. In FIG. 6, the internal protruding element 607 is a wall within the separator chamber 210*sc*, the wall positioned between the first opening 502/210*f* of the separator chamber 210*sc* and the second opening 506/210*g* of the separator chamber 210*sc*. The internal protruding element 607 may have a height of around 7.0 mm, a width of around 24.5 mm and a thickness of around 2.0 mm, so that the internal protruding element 607 may occupy around 10% of the internal volume of the separator chamber 210*sc*. The internal protruding element 607 prevents debris and liquid introduced through the second opening 506/210*g* from entering the pump connector 306. It is preferable that during operation, the debris collector 210*dc* faces the ground; so that as a result of a drop in vacuum levels and under the action of gravity, debris and liquid exiting the third opening 506/210*g* are deposited on an inner wall of the debris collector 210*dc*.

FIG. 6 shows that debris collector 210*dc* has a screw thread 508 which facilitates connection of the debris collector 210*dc* to opening 504 of the separator chamber 210*sc*. In this manner, the debris collector 210*dc* can be easily detached to remove oral debris collected inside the debris collector 210*dc* and also to clean the separator chamber 210*sc*.

Figure 7:
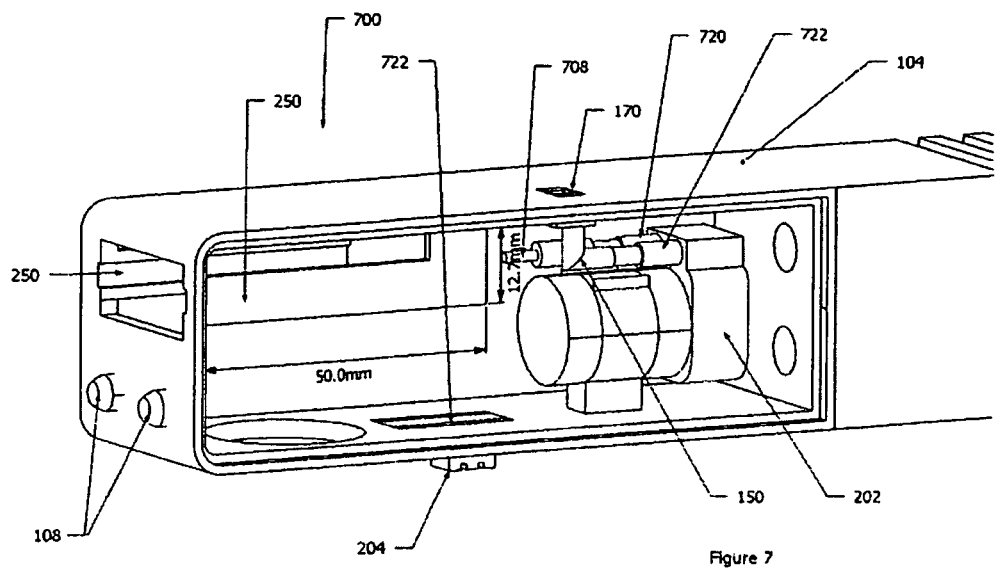
FIG. 7 is a perspective view of a portion of a housing of the oral debris removal device shown in FIGS. 1 and 2.

FIG. 7 is a perspective view of a portion 700 of the housing 104. In FIG. 7, the debris collector chamber 210 is not shown for the sake of simplicity.

The guide rails 250 facilitating insertion of the separator chamber 210*sc* (see FIG. 2) into the housing 104 are clearly shown in FIG. 7.

The switch 204 is coupled to a variable resistive element 722. Although not shown (for the sake of simplicity), the switch 204 is also electrically coupled to the battery compartment 110 (see FIGS. 1 and 2), the suction unit 202 (see FIGS. 1 and 2) and the light source 108 (see FIGS. 1 and 2).

The variable resistive element 722 controls an input power to the suction unit 202. The variable resistive element 722 may be an electrical resistor.

During operation, the magnitude of the variable resistive element 722 is controlled by the switch 204, thereby controlling electrical power supplied to the suction unit 202. The switch 204 has five settings. The first setting deactivates the oral debris removal device 100. The second setting activates the light source 108. The third setting uses a resistance level setting that causes the suction unit 202 to operate at low power. The fourth setting uses a resistance level setting that causes the suction unit 202 to operate at medium power. The fifth setting uses a resistance level setting that causes the suction unit 202 to operate at high power. Example pressure ratings generated by a vacuum created by the suction unit 202 are approximately −560 mbar (high power), −400 mbar (medium power), 300 mbar (low power), while example power ratings of the suction unit 202 are approximately 1.8 watts (high power), 1.5 watts (medium power) and 1.08 watts (low power). The light source 108 remains activated throughout the third to fifth settings.

A filter 708 is connected to an air intake tube 720 of the suction unit 202. The filter 708 traps micro-particles of dust which can shorten the lifespan of the suction unit 202. The air outlet tube 722 of the suction unit 202 is connected to the exhaust port 150, which expels air through the opening 170 when the suction unit 202 is in operation.

Figure 8:
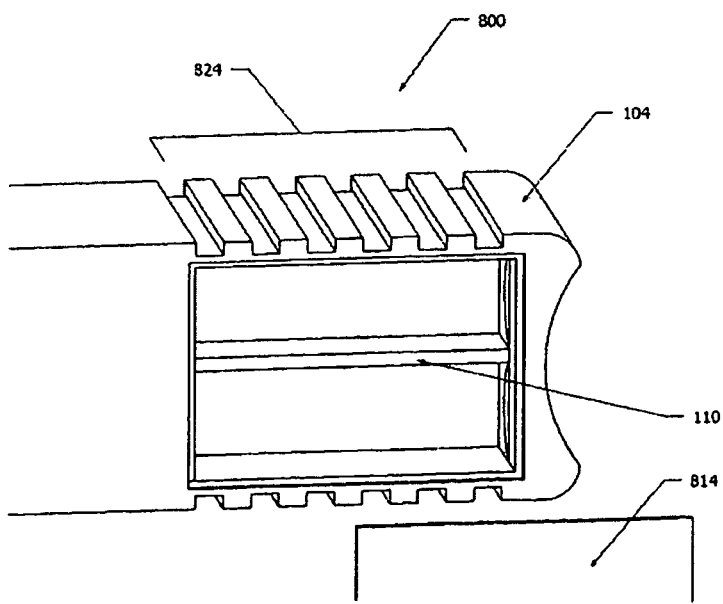
FIG. 8 is a perspective view of a portion of a housing of the oral debris removal device shown in FIGS. 1 and 2.

FIG. 8 is a perspective view of a portion 800 of the housing 104.

FIG. 8 shows that the battery compartment 110 is disposed within the housing 104, wherein the battery compartment 110 has its own battery cover 814. Alternatively, the battery compartment may be separate from the housing 104, wherein the battery compartment is still electrically coupled to the suction unit 202 (see FIGS. 1 and 2) and the light source 108 (see FIGS. 1 and 2). A 9V battery may be used as the power source, although it will be appreciated that other battery types may be used.

An anti-slip surface 824 may be provided on at least a portion of an exterior of the housing 104. As shown in FIG. 8, the anti-slip surface 824 may be a plurality of ridges. Alternatively, the anti-slip surface 824 may be a layer of rubber.

Referring to both FIGS. 7 and 8, the opening 170 (for the exhaust port of the suction unit 202) is disposed between the anti-slip surface 824 of the housing 104 and where the tube 102 (see FIG. 1) is connected to the housing 104.

Figure 9:
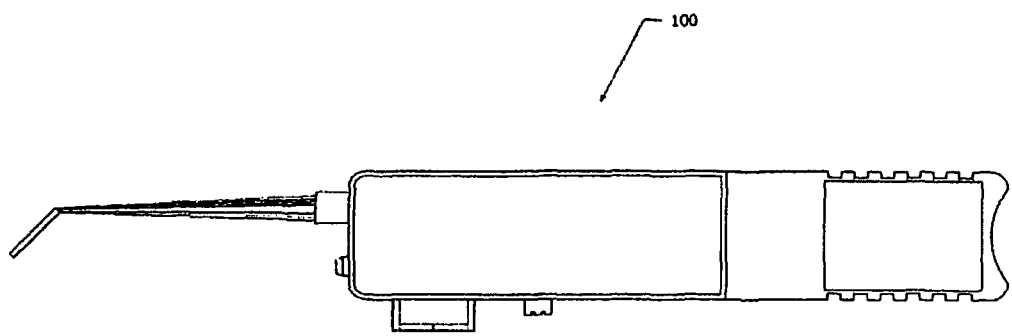
FIG. 9 is a side view of the oral debris removal device shown in FIGS. 1 and 2.
Figure 10:
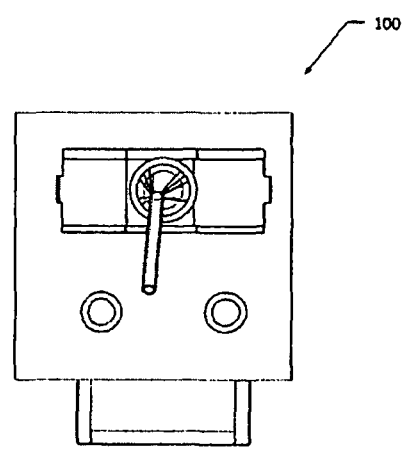
FIG. 10 is a front view of the oral debris removal device shown in FIGS. 1 and 2.

FIG. 9 is a side view of the oral debris removal device 100 shown in FIGS. 1 and 2. FIG. 10 is a front view of the oral debris removal device 100 shown in FIGS. 1 and 2.

FIGS. 11 to 20 relate to an oral debris removal device 1100 according to another embodiment of the present invention.

Figure 11:
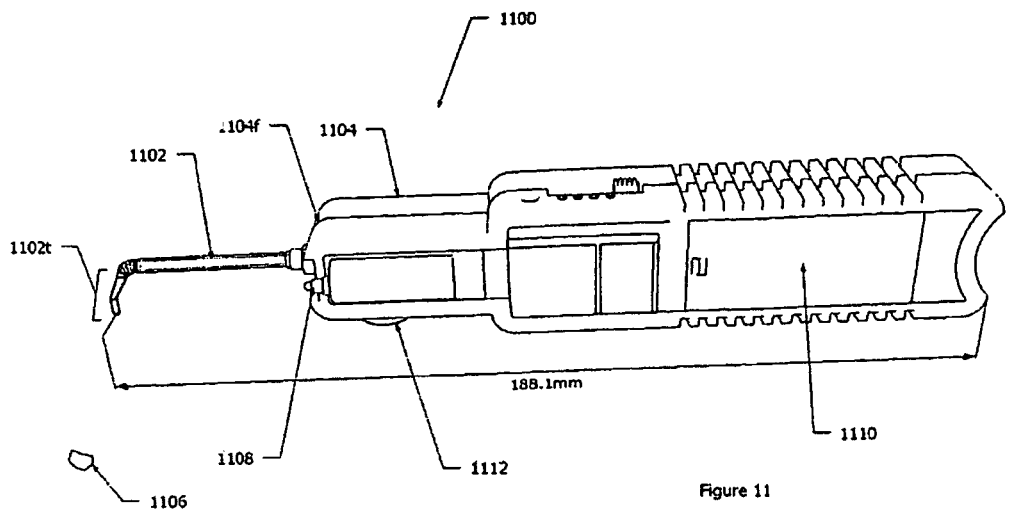
FIG. 11 is a perspective view of an oral debris removal device, according to one embodiment of the present invention.

FIG. 11 is a perspective view of the oral debris removal device 1100 according to one embodiment of the present invention.

The oral debris removal device 1100 is a handheld portable device having suction capability to remove tonsil stones 1106 from the tonsils (not shown) of a human mouth in a safe way without causing lacerations to the tonsils. The oral debris removal device 1100 is designed for self-use (i.e. not requiring the help of a third party) by being operable using one hand and having an integrated light source 1108 (e.g.: a light emitting diode, or LED). The integrated light source 1108 allows illumination of dark crevices, especially located towards the back of a user's mouth, and also allows the oral debris removal device 1100 to be operable with one hand without the need of another hand to hold a separate light source.

The oral debris removal device 1100 allows a person to remove debris which is stuck in his/her tonsils by providing adjustable suction power created by a suction unit (described in further detail later) within the oral debris removal device 1100. Suction occurs through a tube 1102 removably attached to an opening 1104*f* at an end of a housing 1104 for the oral debris removal device 1100. The tube 1102 has a flexible tip portion 1102*t*, thereby facilitating manipulation and bending by a user to place the tip portion 1102*t* of the tube 1102 to the location of a tonsil stone 1106. The tonsil stone 1106 is removed via the suction created by the suction unit. The tonsil stone 1106 is either lodged at an opening of the tip portion 1102*t* of the tube 1102 and remains there due to the suction force, or is sucked through the tube 1102 and collected inside the housing 1104 at a debris collector 1112.

A light source 1108 is provided at one end of the housing 1104, wherein the light source 1108 is directed to illuminate the tip portion 1102*t* of the tube 1102. In FIG. 11, the light source 1108 is shown to be disposed adjacent to the tube 1102, although it is also possible to mount the light source 1108 at another location as long as the light source 1108 can illuminate the tip portion 1102*t* of the tube 1102. Power for the light source 1108 and the suction unit is provided by a battery (not shown in FIG. 11 for the sake of simplicity) in a battery compartment 1110 of the housing 1104. By having its own battery compartment 1110, the oral debris removal device 1100 is portable and therefore the user is not restricted to operating the oral debris removal device 1100 in the vicinity of power mains.

Figure 12:
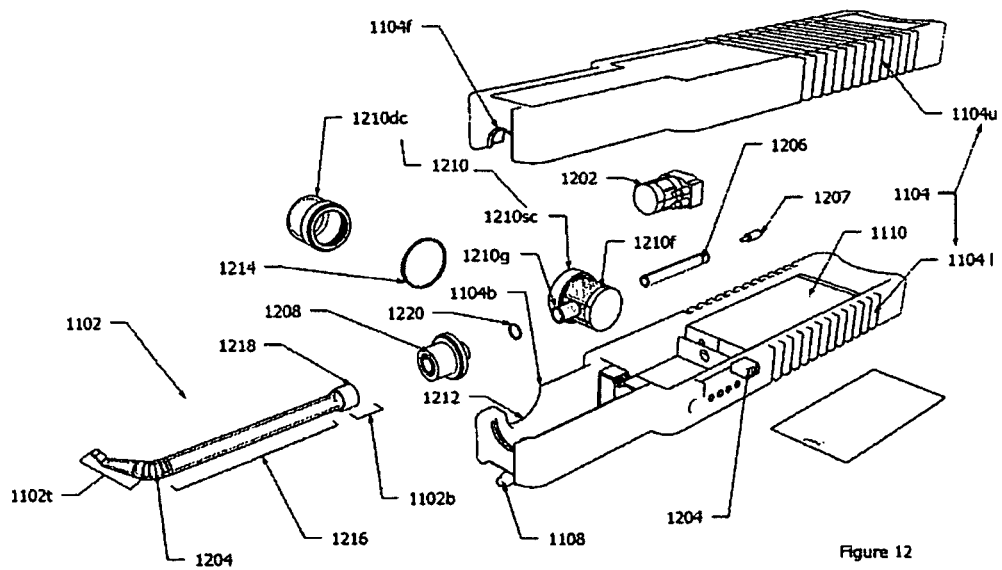
FIG. 12 is an exploded view of the oral debris removal device of FIG. 11.

FIG. 12 is an exploded view of the oral debris removal device 1100 shown in FIG. 11.

The housing 1104 of the oral debris removal device 1100 may be separable into two parts: a lower body 1104*l* and an upper body 1104*u*. The housing 1104 contains the fixtures for the various components of the oral debris removal device 1100, such as a battery compartment 1110, a suction unit 1202 (which may be a diaphragm pump or vacuum pump), a variable switch 1204, a filter 1207 and pump connector 1206, electrical connections (not shown for the sake of simplicity), a light source 1108, a tube adaptor 1208, and a debris collector chamber 1210. The housing 1104 has an opening 1104*f* at one end for the tube 1102 to be inserted and another opening 1212 on a bottom wall 1104*b* for the debris collector chamber 1210 to be inserted. The housing 1104 may be made up of a hard plastic casing.

The oral debris removal device 1100 is provided with a suction unit 1202. In FIG. 12, it is shown that the suction unit 1202 is disposed within the housing 1104, although it would also be possible to connect the suction unit 1202 to the housing 1104. A suitable device such as a diaphragm pump or a vacuum pump may be used for the suction unit 1202.

The tube 1102 is in fluid communication with the suction unit 1202. The tube 1102 has a tip portion 1102*t* adapted to allow introduction of oral debris into the tube 1102 via the tip portion 1102*t*. A light source 1108 is positioned to illuminate the tip portion 1102*t* of the tube 1102 and a region adjacent to the tip portion 1102*t* of the tube 1102. Thus, for example, when the tube 1102 is in contact with the tonsils, the portion of the tonsils that is adjacent to the area of contact will also be illuminated by the light source 1108.

The debris collector chamber 1210 is coupled between an end section of the suction unit 1202 and an end section of the tube 1102. The debris collector chamber 1210 has a first opening 1210*f* (shown more clearly in FIG. 16) to couple the debris collector chamber 1210 to the suction unit 1202 via the pump connector 1206 and through a filter 1207 (see FIG. 16).

The debris collector chamber 1210 further includes a second opening 1210*g*. The second opening 1210*g* facilitates connection between the debris collector chamber 1210, the tube adaptor 1208 and the tube 1102.

The debris collector chamber 1210 may be provided as an integrated unit, although it is shown in FIG. 12 that the debris collector chamber 1210 is provided in two portions, a separator chamber 1210*sc* and a debris collector 1210*dc*. A collector seal 1214 may be used to provide a seal to prevent leakage when the separator chamber 1210*sc* and the debris collector 1210*dc* are connected to each other. The first opening 1210*f* of the debris collector chamber 1210 is provided on the separator chamber 1210*sc*.

The tube 1102 is preferably connected to the housing 1104, although it is sufficient that the tube 1102 is connected to be in fluid communication with the suction unit 1202. In FIG. 12, the tube 1102 is in fluid communication with the suction unit 1202 via the debris collector chamber 1210. The tube 1102 is connected to the debris collector chamber 1210 via a tube adaptor 1208. A base 1102*b* of the tube 1102 has an adaptor 1218 with two protrusions on the surface of the adaptor 1218. The two protrusions match two indentations in an interior wall of the tube adaptor 1208. The tube 1102 is inserted into the tube adaptor 1208 and twisted in a clockwise direction until the protrusions and the indentations align with each other. A chamber seal 1220 may be used to provide a seal to prevent leakage when the tube adaptor 1208 and the separator chamber 1210*sc* are connected to each other.

The tube 1102 may be made of hard clear plastic having an area of inflexion 1204 near the tip 1102*t* of the tube 1102. The inflexion area 1204 provides the tip 1102*t* with a degree of movement relative to a main portion 1216 of the tube 1102. The tip 1102*t* of the tube 1102 may be convex shaped.

Figure 13:
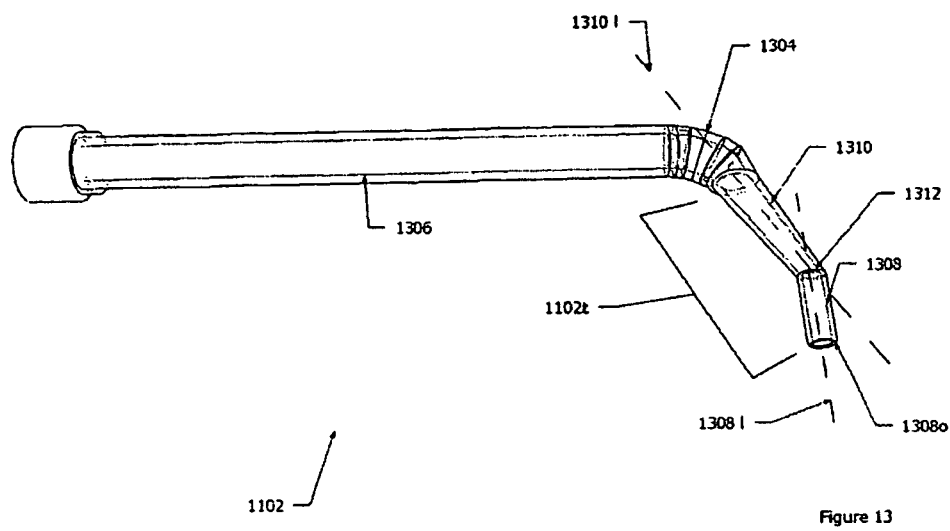
FIG. 13 is a perspective view of a tube of the oral debris removal device of FIGS. 11 and 12.

FIG. 13 is a perspective view of the tube 1102 of the oral debris removal device 1100 shown in FIGS. 11 and 12. The tube 1102 comprises a first portion 1306; and a connecting portion 1304 disposed between the tip portion 1102*t* of the tube 1102 and the first portion 1306. The connection portion 1304 allows misalignment between the tip portion 1102*t* and the first portion 1306.

The tip portion 1102*t* of the tube 1102 further has a first portion 1310 and a second portion 1308. A longitudinal axis 1310*l* of the first portion 1310 is misaligned relative to a longitudinal axis 1308*l* of the second portion 1308.

The diameter of an opening 1308*o* of the second portion 1308 may be around 1.0 mm. The diameter of the interface 1312 between the first portion 1310 and the second portion 1308 may be around 2.0 mm, so that the second portion 1308 has a tapered shape, with opening 1308*o* having a smaller diameter than the diameter at the interface 1312.

The connection portion 1304 may be made from flexible material. The first portion 1306 of the tube 1102 and the tip portion 1102*t* of the tube 1102 may be made from resilient or rigid material.

Figure 14:
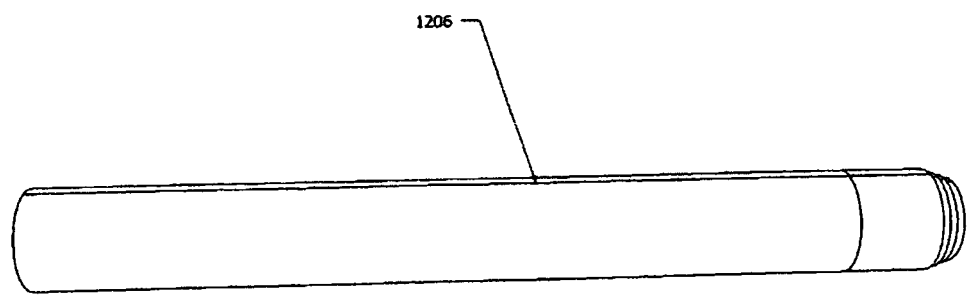
FIG. 14 is a perspective view of a first portion of the tube of the oral debris removal device shown in FIG. 13.

FIG. 14 is a perspective view of the pump connector 1206. The thickness of the wall of the pump connector 1206 may be around 1.0 mm, while the length of the pump connector 1206 may be around 25 mm.

Figure 15:
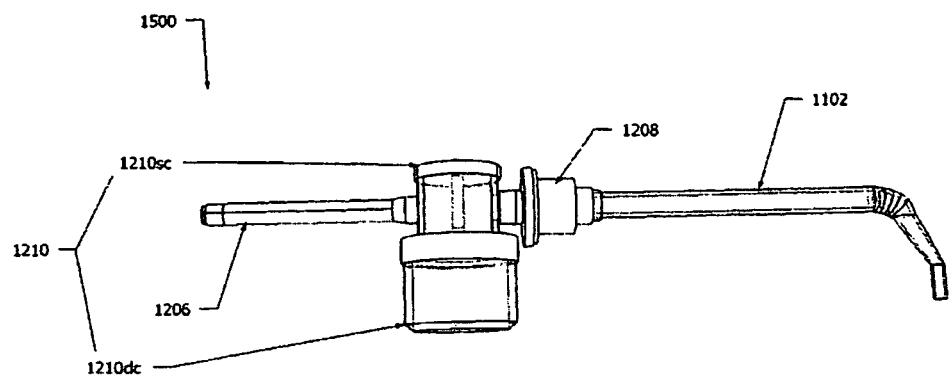
FIG. 15 is a perspective view of a tube unit of the oral debris removal device shown in FIGS. 11 and 12.

FIG. 15 is a perspective view of a tube unit 1500 of the oral debris removal device 1100 shown in FIGS. 11 and 12.

The tube unit 1500 includes the tube 1102, the tube adaptor 1208, the debris collector chamber 1210 and the pump connector 1206.

The debris collector chamber 1210, which includes the separator chamber 1210sc and the debris collector 1210dc, is described in greater detail with reference to FIGS. 16 and 17.

Figure 16:
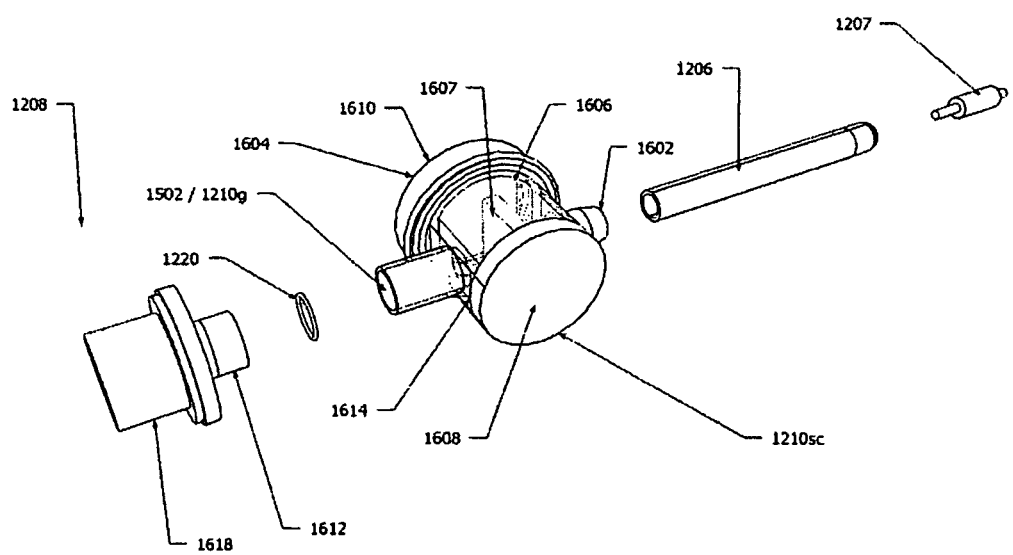
FIG. 16 is an exploded view of a portion of the tube unit of FIG. 15.

FIG. 16 is an exploded view of a portion of the tube unit 1500 of FIG. 15, showing the components of the tube adaptor 1208, the chamber seal 1220, the separator chamber 1210sc and the pump connector 1206.

The separator chamber 1210sc may be made from hard clear plastic. One surface 1608 of the separator chamber 1210sc may have a diameter of around 9.7 mm, while an opposing surface 1610 may have a diameter of around 12.0 mm. The opposing surface 1610 has screw threads 1606 allowing the screwing on of the debris collector 1210dc (see FIG. 17).

The separator chamber 1210sc may have three openings 1602, 1502 and 1604.

The first opening 1602 of the separator chamber 1210sc allows reception of the pump connector 1206 which is used to couple the debris collector chamber 1210 (see FIG. 12) to the suction unit 1202 (see FIG. 12) through a filter 1207. The filter 1207 traps micro-particles of dust which can shorten the lifespan of the suction unit 1202 (see FIG. 12). The first opening 1602 may have a diameter of around 2.6 mm, while the pump connector 1206 may have a length of around 25 mm.

The third opening 1604 of the separator chamber 1210sc may have a diameter of around 12.0 mm.

The second opening 1502 of the separator chamber 1210sc is used to connect the tube adaptor 1208 to the separator chamber 1210sc. The second opening 1502 is formed on a protrusion of around 5.0 mm on a surface 1614 of the separator chamber 1210sc that is facing the tube adaptor 1208. The second opening 1502 has an external diameter of around 3.6 mm. The second opening 1502 of the separator chamber 1210sc is also the second opening 1210g of the debris collector chamber 1210. The chamber seal 1220 is disposed at the connection interface between the tube adaptor 1208 and the separator chamber 1210sc. A rubber o-ring with an internal diameter of around 3.0 mm and an external diameter of around 3.4 mm may be used for the chamber seal 1220.

The separator chamber 1210sc may have an internal protruding element 1607 disposed between where both the suction unit 1202 and the tube 1102 (see FIG. 12) are coupled to the debris collector chamber 1210. The internal protruding element 1607 may be disposed along an air flow path across a space between the end section of the suction unit 1202 and the end section of the tube 1102. The internal protruding element 1607 is adapted to prevent oral debris and liquid exiting the tube 1102 from entering the suction unit 1202. In FIG. 16, the internal protruding element 607 is a wall positioned between the opening 1602 and the opening 1502. The internal protruding element 1607 may have a height of around 6.3 mm, a width of around 6.4 mm and a thickness of around 1.5 mm, so that the internal protruding element 1607 may occupy around 10% of the internal volume of the separator chamber 1210sc. The internal protruding element 1607 prevents debris and liquid exiting the tube adaptor 1208 from entering the first opening 1602 and the pump connector 1206. The separator chamber 1210sc with the internal protruding element 1607 ensures that liquid and debris sucked in through the tube 1102 and into the tube adaptor 1208 are not sucked immediately into the suction unit 1202.

The portion 1612 of the tube adaptor 1208 which faces the separator chamber 1210sc may have a diameter of around 4.0 mm. The portion 1618 of the tube adaptor 1208 which receives the tube 1102 (see FIG. 15) may have a height of around 4.5 mm and a diameter of around 3.0 mm.

Figure 17:
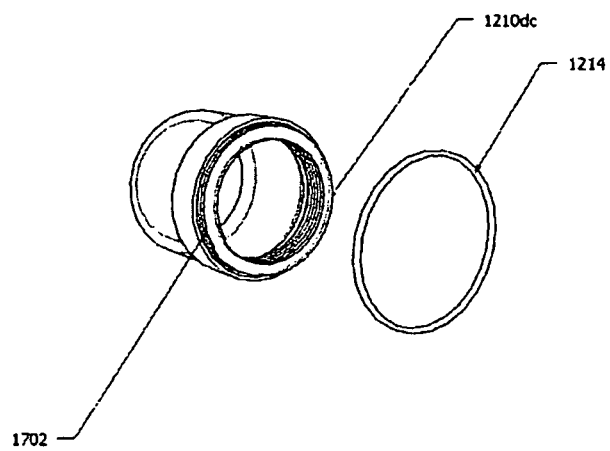
FIG. 17 is an exploded view of a portion of the tube unit of FIG. 15.

FIG. 17 is an exploded view of a portion of the tube unit 1500 of FIG. 15, showing the components of the debris collector 1210dc and the collector seal 1214.

The debris collector 1210dc may be made of hard clear plastic to allow viewing of debris and liquid collected. It is preferable that during operation, the debris collector 1210dc faces the ground; so that as a result of a drop in vacuum levels in the debris collector chamber 1210 and under the action of gravity, debris and liquid exiting the tube 1102 (see FIG. 15) are deposited on an inner wall of the debris collector 1210dc.

A portion 1702 of the debris collector 1210dc has screw threads which correspond to the screw threads 1606 on the separator chamber 1210sc (see FIG. 16). The debris collector 1210dc is connected to the separator chamber 1210sc by twisting the debris collector 1210dc onto the separator chamber 1210sc.

The collector seal 1214 is disposed at the connection interface between the debris collector 1210dc and the separator chamber 1210sc (see FIG. 16). A rubber o-ring with an internal diameter of around 11.4 mm and an external diameter of around 12 mm may be used for the collector seal 1214.

The chamber seal 1220 (see FIG. 16) and the collector seal 1214 ensure that liquid does not leak out of at the respective connection interfaces. The seals 1220 and 1214 also enhance the suction power provided by the suction unit 1202 (see FIG. 12).

Figure 18:
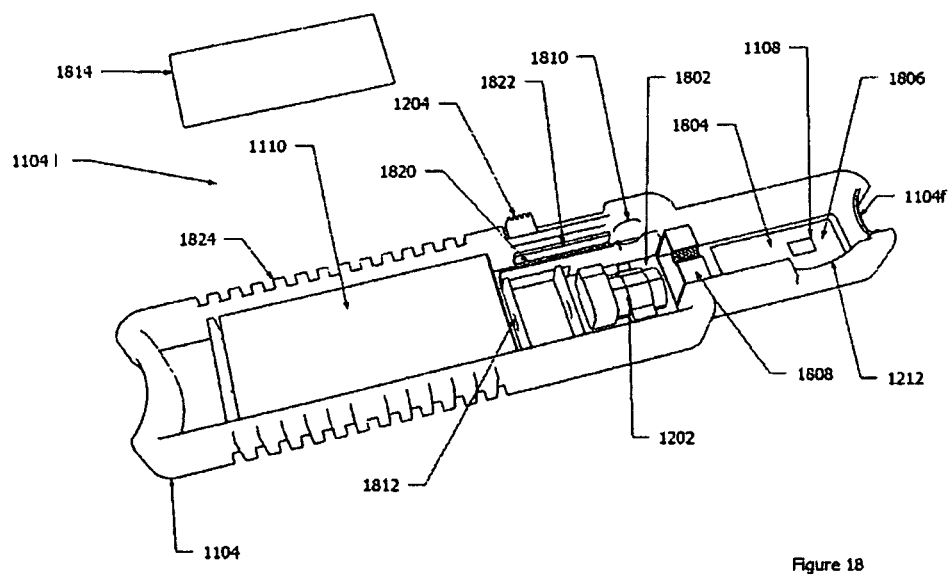
FIG. 18 is a perspective view of a lower body of a housing shown in FIGS. 11 and 12.

FIG. 18 is a perspective view of the lower body 1104l of the housing 1104 shown in FIGS. 11 and 12.

The lower body 1104l has compartments (1110, 1802, 1820, 1804 and 1806 respectively) for a battery, the suction unit 1202, a variable resistive element 1822, the light source 1108, and the separator debris collector chamber 1210 (see FIG. 15) respectively. The lower body 1104l also has openings (1810, 1212 and 1104f respectively) for the exhaust of the suction unit 1202, the debris collector chamber 1210 and the tube adaptor 1208 (see FIG. 15) respectively. The lower body 1104l also contains a tube support 1808 for the pump connector 1206 (see FIG. 5) and electrical cable clearance 1812 for wiring between the battery compartment 1110 to the resistor compartment 1820, the suction unit compartment 1802 and the light source compartment 1804.

FIG. 18 shows that the battery compartment 1110 is disposed within the housing 1104, wherein the battery compartment 1110 has its own battery cover 1814. Alternatively, the battery compartment may be separate from the housing 1104, wherein the battery compartment is still electrically coupled to both the suction unit compartment 1802 and the light source compartment 1804. A 9V battery may be used as the power source, although it will be appreciated that the oral debris removal device 1100 may be configured to accept other battery types.

The resistor compartment 1820 has a variable resistive element 1822. The variable resistive element 1822 is electrically coupled to the suction unit compartment 1802, wherein the variable resistive element 1822 controls an input power to the suction unit 1202 inside the suction unit compartment 1802. The variable resistive element 1822 may be an electrical resistor.

During operation of the oral debris removal device 1100, the magnitude of the variable resistive element 1822 is controlled by the switch 1204. The terminals of the battery compartment 1110 are connected via wire to the variable resistive element 1822 and the switch 1204. Thus, electrical power to the suction unit 1202 is adjusted by moving the switch 1204.

The switch 1204 has five settings. The first setting deactivates the oral debris removal device 1100. The second setting activates the light source 1108 of the light compartment 1804. The third setting uses a resistance level setting that causes the suction unit 1202 in the suction unit compartment 1802 to operate at low power. The fourth setting uses a resistance level setting that causes the suction unit 1202 in the suction unit compartment 1802 to operate at medium power. The fifth setting uses a resistance level setting that causes the suction unit 1202 in the suction unit compartment 1802 to operate at high power. Example pressure ratings generated by a vacuum created by the suction unit 202 are approximately −560 mbar (high power), −400 mbar (medium power), 300 mbar (low power), while example power ratings of the suction unit 202 are approximately 1.8 watts (high power), 1.5 watts (medium power) and 1.08 watts (low power). The light source 1108 in the light compartment 1804 remains activated throughout the third to fifth settings.

The suction unit 1202, when in operation, will suck in air through and expel air through the exhaust port 1810. The exhaust port 1810 is disposed downstream of the suction unit 1202.

In FIG. 18, the exhaust port 1810 may be disposed between an anti-slip surface 1824 of the housing 1104 and where the tube 1102 (see FIG. 1) is connected to the housing 1104.

The anti-slip surface 1824 may be provided on at least a portion of an exterior of the housing 1104. As shown in FIG. 18, the anti-slip surface 1824 may be a plurality of ridges. The distance between each ridge may be about 2 mm. Alternatively, the anti-slip surface 1824 may be a layer of rubber.

Figure 19:
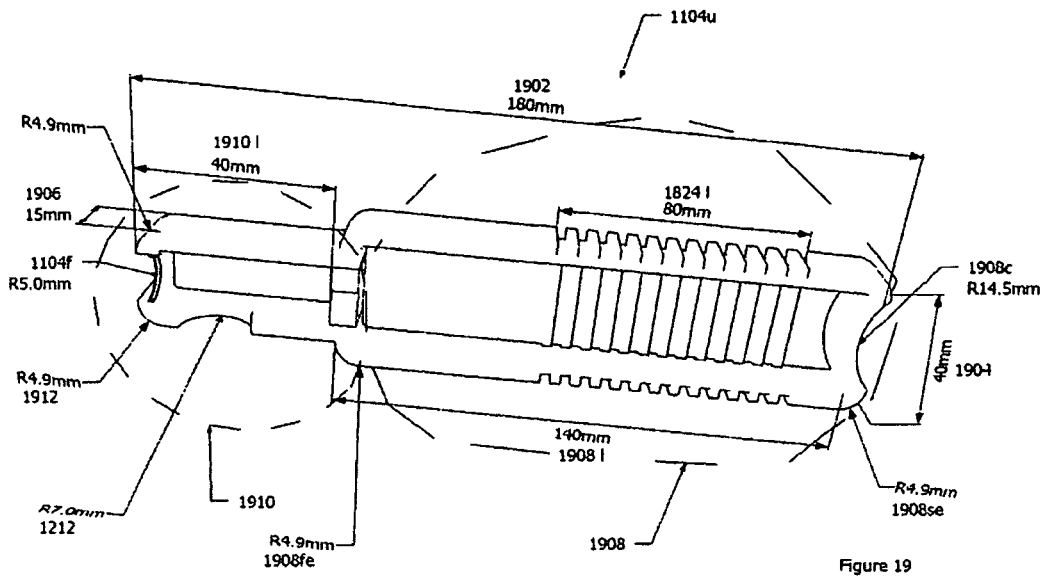
FIG. 19 is a perspective view of an upper body of a housing shown in FIGS. 11 and 12.

FIG. 19 is a perspective view of the upper body 1104u of the housing 1104 shown in FIGS. 11 and 12.

The lower body 1104l and the upper body 1104u, shown in FIGS. 18 and 19 respectively, may be fabricated using plastic injection moulding.

Figure 20:
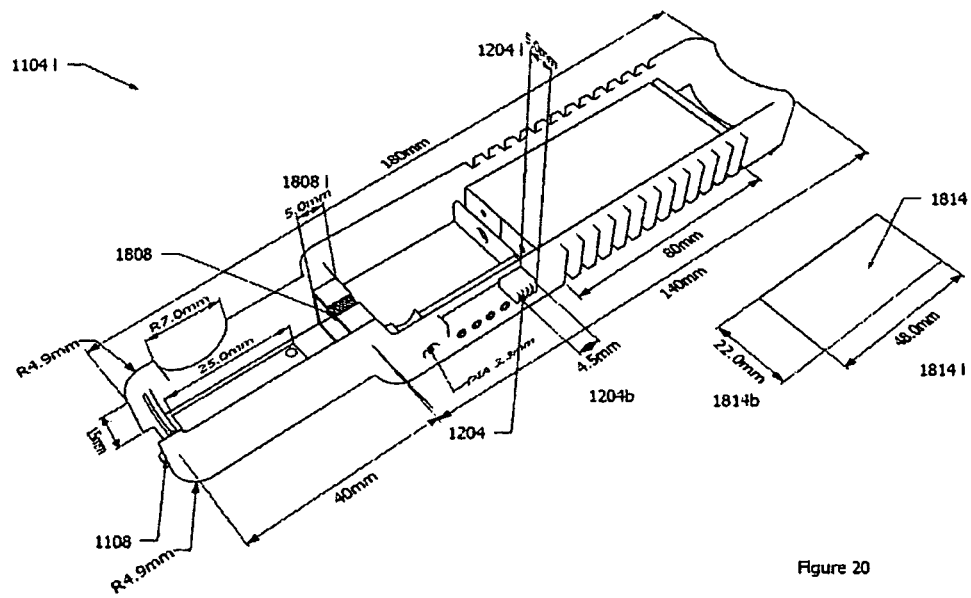
FIG. 20 is another perspective view of a lower body of the housing shown in FIGS. 11 and 12.

FIG. 20 is another perspective view of the lower body 1104l of the housing 1104 shown in FIGS. 11 and 12.

The following paragraphs provide sample illustrative dimensions for the oral debris removal device 1100, with reference to FIGS. 11 and 18 to 20. It will be appreciated that the dimensions provided are for illustrative purposes, where other appropriate dimensions may be used to realize the oral debris removal device 1100. It will also be appreciated that the oral debris removal device 100 (shown in FIGS. 1 to 10) may also have similar dimensions to the oral debris removal device 1100, whereby sample dimensions (provided in FIGS. 1, 4B and 7) for the oral debris removal device 100 are for illustrative purposes.

The length 1902 of the upper body 1104u may be around 180 mm, the breadth 1904/818 of the upper body 1104u may be around 40 mm, while the thickness 1906 of the upper body 1104u may be around 15 mm. It will be appreciated that the housing 1104 will also have the same length and breadth dimensions, while the thickness of the housing 1104 may be around 30 mm (i.e. twice the thickness of the upper body 1104u).

The housing 1104 has a rear portion 1908 and a forward portion 1910.

The rear portion 1908 may extend a length 1908l of around 140 mm. The anti-slip surface 1824 may extend a length 1824l of around 80 mm along the length 1908l of the rear portion 1908. The exhaust port 1810 may have a diameter of around 3.3 mm. At the adjoining portion between the rear portion 1908 and the forward portion 1910, a first end 1908fe of the rear portion 1908 may have a radius of around 4.9 mm. A similar structural curvature with a radius of around 4.9 mm may be present at a second end 1908se which is opposite to the first end 1908fe. Another curvature 1908c, having a radius of around 14.5 mm, may be present at the second end 1908se and aligned with the two 4.9 mm curvatures present at the second end 1908se.

The forward portion 1910 may extend a length 1910l of around 40 mm. The light source 1108 may extend a distance of around 25 mm along the length 1910l of the forward portion 1910. The opening 1104f, which accommodates the tube adaptor 1218 (see FIG. 12), may be located at the forward portion 1910 of the housing 1104. The opening 1212, from which a portion of the debris collector 1210dc (see FIG. 15) protrudes, is also located at the forward portion 1910 of the housing 1104. The opening 1104f and the opening 1212 may have radii of around 5.0 mm and around 7.0 mm respectively. A segment 1912 of the forward portion 1910 that is adjacent to the opening 1104f may have a radial curvature of around 4.9 mm.

Turning to the internal dimensions of the housing 1104, the battery cover 1814 may have a length 1814l of around 48 mm and a breadth 1814b of around 22 mm. The tube support 1808 may extend a distance 1808l of around 5 mm and accommodate tubes of having a diameter of around 2.6 mm. The switch 1204 may have a length 1204l of around 5 mm and a breadth 1204b of around 4.5 mm.

The invention claimed is:

1. A tonsil debris removal device comprising:
   a suction unit;
   a tube in fluid communication with the suction unit, the tube having a tip portion adapted to allow introduction of debris into the tube via the tip portion;
   a light source positioned to illuminate the tip portion of the tube and a region adjacent to the tip portion of the tube;
   a housing, upon which the suction unit is provided;
   a debris collector chamber coupled between an end section of the suction unit and an end section of the tube; and
   wherein the debris collector chamber comprises a first opening to couple the debris collector chamber to the suction unit; and a filter covering the first opening.

2. The tonsil debris removal device of claim 1, wherein the suction unit is disposed within the housing.

3. The tonsil debris removal device of claim 1, wherein the suction unit is connected to the housing.

4. The tonsil debris removal device of claim 1, wherein the suction unit comprises any one or more of a diaphragm pump and a vacuum pump.

5. The tonsil debris removal device of claim 1, wherein the debris collector chamber comprises an internal protruding element disposed along an air flow path across a space between the end section of the suction unit and the end section of the tube, the internal protruding element adapted to prevent debris and liquid exiting the tube from entering the suction unit.

6. The tonsil debris removal device of claim 1, wherein the tube is connected to the housing.

7. The tonsil debris removal device claim 1, wherein the tube comprises a first portion; and a connecting portion disposed between the tip portion of the tube and the first portion, the connection portion allowing misalignment between the tip portion and the first portion.

8. The tonsil debris removal device claim 1, wherein the tip portion of the tube comprises a first portion and a second portion, wherein a longitudinal axis of the first portion is misaligned relative to a longitudinal axis of the second portion.

9. The tonsil debris removal device of claim 7, wherein the connection portion is made from flexible material.

10. The tonsil debris removal device of claim 7, wherein the first portion of the tube and the tip portion of the tube are made from resilient or rigid material.

11. The tonsil debris removal device claim 1, further comprising a battery compartment, the battery compartment being electrically coupled to both the suction unit and the light source.

12. The tonsil debris removal device of claim 11, wherein the battery compartment is disposed within the housing.

13. The tonsil debris removal device claim 1, wherein the light source is disposed adjacent to the tube.

14. The tonsil debris removal device of claim 1, wherein the light source comprises a light emitting diode.

15. The tonsil debris removal device of claim 1, wherein at least a portion of an exterior of the housing is provided with an anti-slip surface.

16. The tonsil debris removal device of claim 1, further comprising a variable resistive element electrically coupled to the suction unit, wherein the variable resistive element controls an input power to the suction unit.

17. The tonsil debris removal device of claim 1, the housing further comprising an exhaust port, the exhaust port disposed downstream of the suction unit.

18. The tonsil debris removal device of claim 17, wherein the exhaust port is disposed between the anti-slip surface of the housing and wherein the tube is connected to the housing.

* * * * *